United States Patent [19]

Hyakumura

[11] Patent Number: 4,831,276
[45] Date of Patent: May 16, 1989

[54] APPARATUS FOR MEASURING REFLECTIVITY

[75] Inventor: Kazushi Hyakumura, Hachiouji, Japan

[73] Assignee: Olympus Optical Co., Ltd., Tokyo, Japan

[21] Appl. No.: 159,434

[22] Filed: Feb. 17, 1988

Related U.S. Application Data

[63] Continuation of Ser. No. 855,474, Apr. 24, 1986, abandoned.

[30] Foreign Application Priority Data

Apr. 25, 1985 [JP] Japan .................... 60-89573

[51] Int. Cl.$^4$ .............................................. G01N 21/86
[52] U.S. Cl. ..................................... 250/571; 356/445
[58] Field of Search ............... 250/571, 559; 350/319, 350/525, 527; 356/445-448, 124

[56] References Cited

U.S. PATENT DOCUMENTS

| | | | |
|---|---|---|---|
| 3,396,266 | 8/1968 | Max et al. ........................... | 250/559 |
| 3,874,799 | 4/1975 | Isaacs et al. ........................ | 356/236 |
| 4,062,623 | 12/1977 | Suzuki et al. ...................... | 356/445 |
| 4,097,751 | 6/1978 | Egan et al. ......................... | 250/571 |
| 4,198,571 | 4/1980 | Sheppard ............................ | 250/571 |
| 4,199,219 | 4/1980 | Suzki .................................. | 356/445 |
| 4,368,982 | 1/1983 | Van Arnam et al. .............. | 250/571 |
| 4,636,080 | 1/1987 | Feldman ............................. | 356/401 |

FOREIGN PATENT DOCUMENTS 5213378 7/1975 Japan .
54-133180 10/1979 Japan .

Primary Examiner—David C. Nelms
Attorney, Agent, or Firm—Cushman, Darby & Cushman

[57] ABSTRACT

In order to insure a high degree of precision of measurement with a simple structure, the apparatus for measuring reflectivity employs an objective lens, a half-mirror disposed rearwardly of the objective lens and a light source means disposed on one of the optical paths so split by the half-mirror for emitting an annular bundle of light. A fine aperture stop is disposed on the other optical path so split by the half-mirror. A light-responsive device is disposed rearwardly of the fine aperture stop, a memory is coupled to the light-responsive device and a mathematical operation device is connected to the memory. An indicating device is connected to the mathematical operation device. An annular bundle of light is collected onto an examination surface via the half-mirror and the objective lens, and that the reflection light produced at the examination surface is caused to impinge onto the light-responsive device via the objective lens, the half-mirror and the fine aperture stop. In order to eliminate harmful reflection light coming from the surface of the objective lens, and to prevent a loss of amount of light at the half-mirror, polarizers are disposed one on the light source side and the other on the light-responsive device side of the half-mirror in such a way that their polarization planes cross each other at right angles, and that a ¼ wave plate is provided between the objective lens and the examination surface.

9 Claims, 2 Drawing Sheets

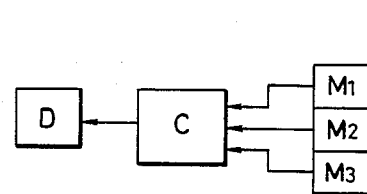
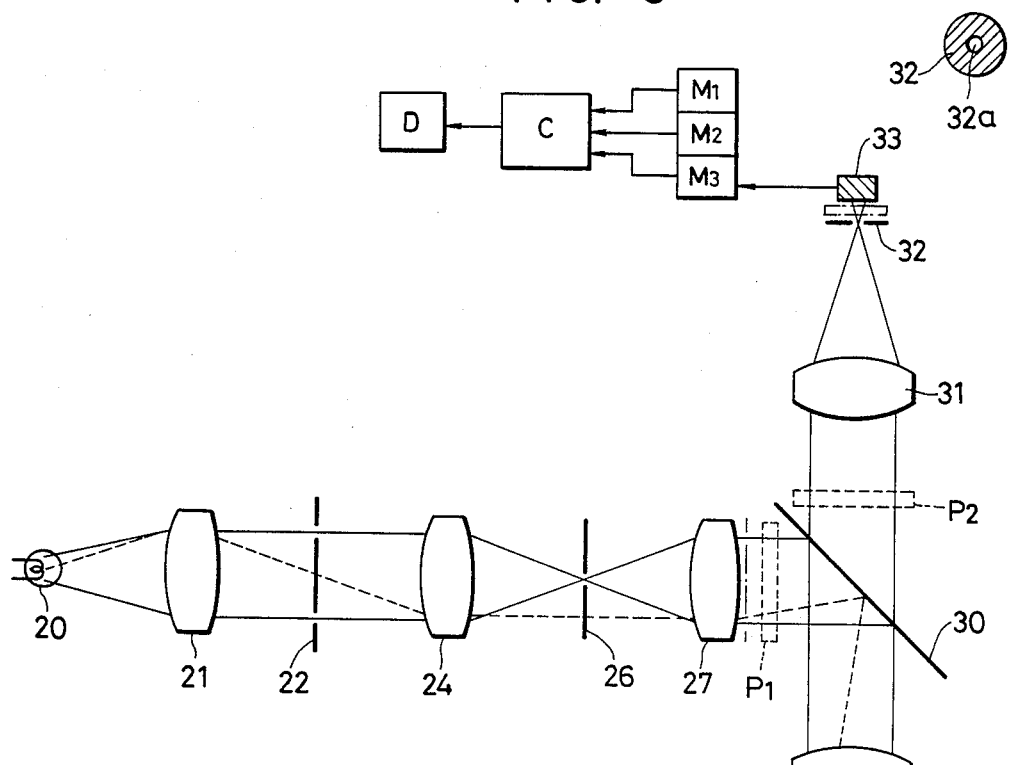
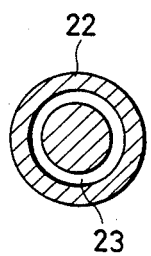
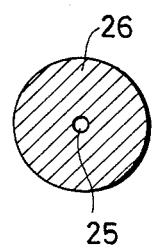
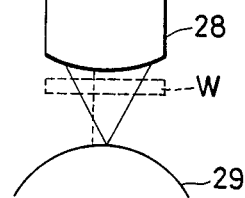

APPARATUS FOR MEASURING REFLECTIVITY

This is a continuation of application Ser. No. 855,474, filed Apr. 24, 1986, which was abandoned upon the filing hereof.

BACKGROUND OF THE INVENTION (a) Field of the Invention:

The present invention relates to an apparatus for measuring reflectivity.

(b) Description of the prior art:

Anti-reflection coating technique is an important art indispensable for various kinds of optical systems. Without the application of this specific technique, there arises the inconvenience that lens systems such as zoom lens and objective lens of a high-grade microscope which are comprised of a number of component lens would develop a substantial drop of light-transmittance, and such lens systems are never acceptable for practical use. In order to confirm that the lens system is provided with a proper anti-reflection coating, it is necessary to conduct an actual measurement of the reflectivity of the anti-reflection film formed on the lens surface. Although reflectivity measuring devices have been known since a long time ago, devices of this kind, in general, allow the measurement of reflectivity of only a planar surface, so that it has been the usual practice to use, as a test-piece, a planar glass plate having the formation of an anti-reflective film on the surface thereof which is produced thereon under the same condition as would be formed on the surface of a lens, and to measure the reflectivity of the test-piece. With such a manner of measurement employed in the past, the actual reflectivity of the anti-reflection film formed on a lens surface is not known. The reflection light which comes from the rear surface of the test-piece is mingled with the measurement light so that the prior art measuring devices had the drawback represented by a low degree of precision of measurement.

Therefore, the present inventors have disclosed, in Japanese Patent Preliminary Publication No. Sho 54-133180, a reflectivity measuring apparatus which allows the measurement of the reflectivity of a curved surface and which prevents the intrusion of the reflection light coming from the rear surface of a lens. This apparatus has such a construction as shown in FIG. 1. That is, in FIG. 1, reference numerals 1 and 2 represent two objective lenses which are disposed in such a way that their optical axes 3 and 4 cross each other at right angles. At the focal positions of these two lenses, there are disposed a reference surface 5 and a surface 6 for examination, respectively, which will hereunder be called simply an examination surface 6. In addition, a reflecting mirror 7 having reflecting surfaces on both faces thereof is provided off-axially, i.e. outside of the optical axes, of these lenses 5 and 6. And, among the two monochromatic light beams which are incident to the lens 1 in parallel with the optical axis 3 thereof, the beam 8 is reflected at the rear surface of the reflecting mirror 7, and is collected by the objective lens 2 to enter obliquely onto the examination surface 6, and the light reflected at the examination surface 6 passes through the objective lens 2 and advances in parallel with the optical axis 4, and via a light-collecting lens 10 which is disposed coaxially with the objective lens 2, it is collected onto a light-receiving device 12 after passing through a stop 11. The light beam 9, on the other hand, is collected onto the reference surface 5 by the objective lens 1, and the reflection light coming from the reference surface 5 passes through the objective lens 1 and advances in parallel with the optical axis 3, and after being reflected at the reflecting mirror 7, it impinges onto the light-receiving device 12 in the same manner as does the light beam 8.

With this arrangement mentioned above, the measurement beam of light is squeezed into a fine spot light at the examination surface 6 and also at the reference surface 5, so that the reflectivity at a planar surface as well as at a curved surface can both be measured. Also, because the measurement light beam enters obliquely, it will be noted from FIG. 2 that the surface reflection light and the rear surface reflection light follow different optical paths relative to each other. Therefore, it is possible to eliminate the rear surface reflection light by the stop 11 which is provided in front of the light-receiving device 12.

According to the above-mentioned prior art example, however, there have been encountered the following problems, which are:

(a) because two objective lenses are employed, the optical system becomes complicated in construction and tends to have a large size; and (b) because of the employment of a fine beam of light which is incident off-axially of the objective lens, there arises an insufficiency of the intensity of the measurement light, and accordingly it is affected by noises, and the degree of precision of measurement has tended to become degraded.

SUMMARY OF THE INVENTION

It is, therefore, a primary object of the present invention to provide an apparatus for measuring reflectivity, which is simplier in construction than in the prior art and yet which provides for a high degree of precision of measurement.

The apparatus for measuring reflectivity according to the present invention comprises an objective lens, an optical path splitting device disposed rearwardly of the objective lens, a light source disposed on one of the optical paths so split by said optical path splitting device for emitting an annular bundle of light; a fine aperture stop disposed on the other optical path so split by said optical path splitting device; and a light-responsive device disposed rearwardly of said fine aperture stop, and is arranged to be operative so that the bundle of light emitting from said light source is collected, by said objective lens via said optical path splitting device onto an examination surface and that the reflection light produced by said examination surface is received by said light-responsive device via said objective lens, said optical path splitting device and said fine aperture stop. Since there is provided only one objective lens, the arrangement of this apparatus is simplified. Also, because an annular bundle of light is used, a sufficient amount of light can be obtained.

This and other objects as well as the features and the advantages of the present invention will be apparent from the following detailed description of the preferred embodiment when taken in conjunction with the accompanying drawings.

BRIEF DESCRIPTION OF THE DRAWINGS

FIG. 3 is an illustration showing an embodiment of the apparatus for measuring reflectivity according to the present invention.

FIG. 4 is a front view of an annular aperture stop employed in the apparatus shown in FIG. 3.

FIG. 5 is a front view of the aperture stop 26 employed in the apparatus of FIG. 3.

FIG. 6 is a front view of an aperture stop 32 employed in the apparatus of FIG. 3.

DETAILED DESCRIPTION OF THE PREFERRED EMBODIMENT

Figure 1:
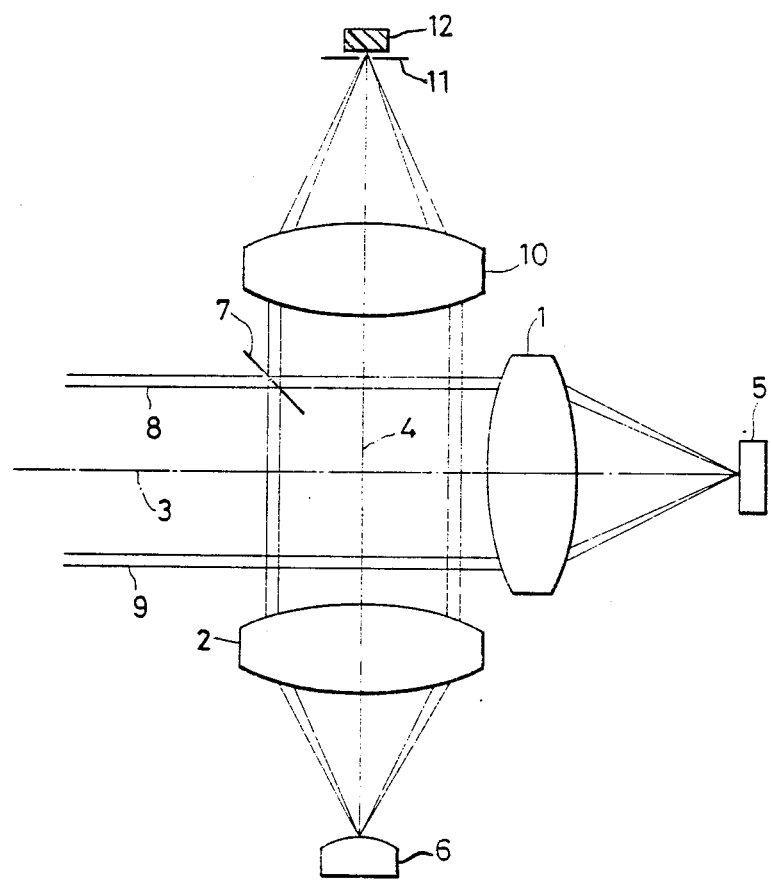
FIG. 1 is an illustration showing a conventional reflectivity measuring device.

In FIGS. 3 to 6, reference numeral 20 represents a light source; 21 a light-collecting lens; and 22 an annular aperture stop having an annular aperture 23 disposed at the position of the image of the light source formed by said light-collecting lens 21. A relay lens 24 is disposed in such a way that its front-side focal point coincides with the annular aperture stop 22, and that an aperture stop 26 having a pin-hole 25 is provided at the rearward focal point of the relay lens 24. A relay lens 27 is disposed in such a way that its front-side focal point is in agreement with the aperture stop 26 and that its rear-side focal point coincides with the rear-side focal point of an objective lens 28. Numeral 29 represents an examination surface, and numeral 30 represents a half-mirror. Numeral 31 denotes a light-collecting lens, and an aperture stop 32 having a pin-hole 32a which is slightly larger in size than the image of the pin-hole 25 is provided at the rear-side focal point of the light-collecting lens 31. A light-responsive device 33 such as a photomultiplier or photodiode is disposed immediately behind the aperture stop 32. Symbols $M_1$ to $M_3$ represent memories; C denotes a processing unit; and D represents an indicating device.

The apparatus for measuring reflectivity according to the present invention is constructed as stated above. Therefore, the bundle of light emitting from the light source 20 is rendered to an annular bundle of light by the annular aperture 23 of the annular aperture stop 22, and the resulting light bundle is collected onto the aperture stop 26 by the relay lens 24, and is squeezed into a fine light spot by the pin-hole 25. The bundle of light emitting from the pin-hole 25 is rendered to a parallel annular bundle of light by the relay lens 27, and is reflected by the half-mirror 30 to be collected onto the examination surface 29 by the objective lens 28. The reflection light produced at the examination surface 29 is rendered to a parallel annular bundle of light by the objective lens 28, and after passing through the half-mirror 30, it is collected onto the aperture stop 32 by the light-collecting lens 31, and after passing through the pin-hole 32a, it impinges onto the light-responsive device 33.

Figure 2:
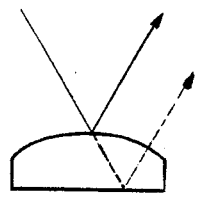
FIG. 2 is an illustration showing the directions of reflection of light at both the front surface and the rear surface of an object requiring examination in the conventional device shown in FIG. 1.

This optical system employs an annular bundle of light, and accordingly it is possible to provide an abundant amount of measurement light. Also, the reflection light of the object under examination coming from the rear side of the examination surface (see FIG. 2) is projected as a blurred image onto the aperture stop 32. However, because the illuminating bundle of light is of an annular shape, said reflection light will blur in the form of a ring. For this reason, the reflection light will not pass through the pin-hole 32a.

Next, explanation will be made of the method of measuring the reflectivity of the examination surface 29 by means of this reflectivity measuring apparatus.

To begin with, under the state that nothing is placed at the light-collecting position of the objective lens 28, the output within a certain length of time T of the light-responsive device 33 is stored in the memory $M_1$. Then, the reference surface 5 (see FIG. 1) is placed at the light-collecting position of the objective lens 28, and the output of the light-responsive device 33 within the same certain length of time T as that mentioned just above is stored in the memory $M_2$. Further, in place of the reference surface, the examination surface 29 is again placed at the light-collecting position of the objective lens 28, and the output of the light-responsive device 33 within a certain length of time T is stored in the memory $M_3$. These three storage values are delivered out to the mathematical operation device C, and after subtracting the storage value of the memory $M_1$ from the storage values of the memories $M_2$ and $M_3$, the reflection characteristic of the examination surface 29 is sought in accordance with a predetermined program, and the result thereof is indicated on an indicating device.

Here, it should be noted that the storage value of the memory $M_1$ is comprised of unwanted external light, dark current of the light-responsive device 33 or like lights, so that this value is subtracted and then the reflectivity is sought. This means that a mathematical operation of reflectivity is carried out in the state that harmful signal components have been eliminated. Thus, together with the abundancy of measurement light, it is possible to perform a measurement of reflectivity with a very high degree of precision.

By arranging so that the half-mirror 30 is comprised of a polarization beam splitter and that a pair of polarizers $P_1$ and $P_2$ having polarization plane which cross each other at right angles are disposed on the light source side and on the light-responsive device side of the above-mentioned beam splitter, and further that a ¼ wave plate W is provided between the objective lens 28 and the examination surface 29 as shown by a broken line in FIG. 3, it is possible to eliminate harmful light caused by the reflection at the lens surface of the objective lens 28, and also to prevent the loss of amount of light at the half-mirror 30, whereby measurements with a further elevated degree of precision become feasible.

In the above-described embodiment, the annular aperture stop 22 is provided on the light source side of the aperture stop 26. However, this annular aperture stop 22 may be disposed between the aperture stop 26 and the half-mirror 30 as shown by a chain line in FIG. 3. Furthermore, by disposing a spectroscope between the aperture stop 32 and the light-responsive device 33 as shown by a chain line, it is possible to measure the spectroscopic reflectivity of the examination surface also.

Also, in the above-mentioned embodiment, arrangement is provided so that the output of the light-responsive device within a certain length of time is stored in each memory. It should be noted, however, that such an arrangement is not always necessary depending on the type of the method of measurement employed.

What is claimed is:

1. An apparatus for measuring reflectivity of a front surface of an examination object which is a transparent body having a front surface and a rear surface and which reflects light from both the front and rear surface, comprising:

an objective lens for collecting light on the front surface of said examination object;

an optical path splitting device disposed rearwardly of said objective lens in order to split an optical path formed by said objective lens into a first optical path and a second optical path;

light source means disposed on said first optical path for emitting an annular bundle of light;

a first fine aperture stop disposed on said second optical path;

a light-responsive device disposed rearwardly of said first fine aperture stop; and mathematical operation means for providing a reflectivity value from output values of said light-responsive device, said annular bundle of light emitting from said light source means being collected so as to become a point at a predetermined position via said optical path splitting device and said objective lens, and said first fine aperture stop being positioned so that, in that state in which the front surface of said examination object is placed at said predetermined position, reflection light produced from said front, examination surface can again collected so as to become a point in a position of said first fine aperture stop via said objective lens and said optical path splitting device and impinges upon said light-responsive device through said fine aperture stop, and reflection light produced from a surface other than said front, examination surface is an annular bundle of light which substantially does not pass through said fine aperture stop.

2. An apparatus for measuring reflectivity according to claim 1, in which:

said mathematical operation means is constructed to measure reflectivity of the front surface of said examination object in accordance with a first output value of said light-responsive device under the state that said examination object is not placed at the predetermined position, a second output value of said light-responsive device under the state that a reference surface is placed, instead of the front surface of said examination object, at the predetermined position, and a third output value derived from said light-responsive device by the light reflected from the front surface of said examination object.

3. An apparatus for measuring reflectivity according to claim 2, in which:

said first output value is an output value derived from said light-responsive device as a result of making measurement with said light-responsive device for a certain length of time under the state that said examination object is not placed at the predetermined position, said second output value is an output value derived from said light-responsive device as a result of making measurement with said light-responsive device for the same certain length of time under the state that said reference surface is placed, instead of the front surface of said examination object, as the predetermined position, and said third output value is an output value derived from said light-responsive device as a result of measuring the light reflected from the front surface of said examination object with said light-responsive device for the same certain length of time.

4. An apparatus for measuring reflectivity according to claim 2, in which:

said mathematical operation means further operate to calculate a first difference value by subtracting said first output value from said second output value and a second difference value by subtracting said first output value from said third output value and to determine the reflectivity of the examination surface from said first and second difference values.

5. An apparatus for measuring reflectivity according to claim 4, in which:

said mathematical operation means comprise:
first memory means for storing said first output value;
second memory means for storing said second output value;
third memory means for storing said third output value.

6. An apparatus for measuring reflectivity according to any one of claims 1 through 5 in which:

said light source means comprises:
a light source;
a light-collecting lens disposed adjacent to said light source;
an annular aperture stop disposed on an optical axis of said light-collecting lens at a light source image forming position;
a first relay lens disposed so that its front-side focal position coincides with the position of said annular aperture stop;
a second fine aperture stop disposed at a rear-side focal position coincides with the position of said second fine aperture stop and that its rear-side focal position coincides with the rear-side focal position of said objective lens.

7. An apparatus for measuring reflectivity according to any of claims 1 through 5 further comprising:

a first polarizing device disposed on said first optical path;
a second polarizing device disposed on said second optical path having a polarizing surface crossing the polarization plane of said first polarizing device at right angles; and
a ¼ wave plate disposed between said objective lens and said examination surface.

8. An apparatus for measuring reflectivity according to any one of claims 1 through 5 further comprising:

a spectroscope disposed between said first fine aperture stop and light-responsive device.

9. An apparatus for measuring reflectivity according to any one of claim 1 through 5, in which said light source means comprising:

a light source;
a second fine aperture stop disposed at a position of forming the image of said light source;
a relay lens disposed so that its front-side focal position coincides with the position of said second fine aperture stop and that its rear-side focal position coincides with the position of the rear-side focal position of said objective lens; and
an annular aperture stop disposed at a position on the side opposite to said second fine aperture stop relative to said relay lens.

* * * * *